(12) United States Patent
He et al.

(10) Patent No.: US 12,265,066 B2
(45) Date of Patent: Apr. 1, 2025

(54) IMAGING METHOD AND SYSTEM FOR RESIDUAL STRESS OF BASIN INSULATOR, AND METHOD FOR PREPARING TEST BLOCK

(71) Applicants: ELECTRIC POWER SCIENCE & RESEARCH INSTITUTE OF STATE GRID TIANJIN ELECTRIC POWER COMPANY, Tianjin (CN); STATE GRID TIANJIN ELECTRIC POWER COMPANY, Tianjin (CN); STATE GRID CORPORATION OF CHINA, Beijing (CN)

(72) Inventors: Jin He, Tianjin (CN); Chun He, Tianjin (CN); Songyuan Li, Tianjin (CN); Qinghua Tang, Tianjin (CN); Chi Zhang, Tianjin (CN); Rong Chen, Tianjin (CN); Qi Zhao, Tianjin (CN); Jin Li, Tianjin (CN); Xiaobo Song, Tianjin (CN); Yue Han, Tianjin (CN); Meng Cao, Tianjin (CN); Lin Li, Tianjin (CN); Suya Li, Tianjin (CN); Yanwei Dong, Tianjin (CN); Zhengzheng Meng, Tianjin (CN)

(73) Assignees: ELECTRIC POWER SCIENCE &RESEARCH INSTITUTE OF STATE GRID TIANJIN ELECTRIC POWER COMPANY, Tianjin (CN); STATE GRID TIANJIN ELECTRIC POWER COMPANY, Tianjin (CN); STATE GRID CORPORATION OF CHINA, Beijing (CN)

(*) Notice: Subject to any disclaimer, the term of this patent is extended or adjusted under 35 U.S.C. 154(b) by 0 days.

(21) Appl. No.: 18/724,989

(22) PCT Filed: Oct. 8, 2023

(86) PCT No.: PCT/CN2023/123348
§ 371 (c)(1),
(2) Date: Jun. 27, 2024

(87) PCT Pub. No.: WO2024/131209
PCT Pub. Date: Jun. 27, 2024

(65) Prior Publication Data
US 2025/0067647 A1 Feb. 27, 2025

(30) Foreign Application Priority Data
Dec. 21, 2022 (CN) .......................... 202211644860.X (51) Int. Cl.
*G01N 3/12* (2006.01)
*G01N 1/44* (2006.01)
(Continued)

(52) U.S. Cl.
CPC ................. *G01N 3/12* (2013.01); *G01N 1/44* (2013.01); *G01N 29/0654* (2013.01);
(Continued)

(58) Field of Classification Search
CPC ........ G01N 3/12; G01N 1/44; G01N 29/0654; G01N 29/07; G01N 29/227; G01N 33/442;
(Continued)

(56) References Cited

U.S. PATENT DOCUMENTS

| 4,926,692 A | * | 5/1990 | Brokowski | ............ | G01N 29/07 |
| | | | | | 73/597 |
| 5,474,070 A | * | 12/1995 | Ophir | ..................... | G01N 29/07 |
| | | | | | 600/437 |

(Continued)

FOREIGN PATENT DOCUMENTS

| CN | 103439248 A | 12/2013 |
| CN | 109959477 A | 7/2019 |

(Continued)

OTHER PUBLICATIONS

Chinese Office Action for Chinese Application No. 202211644860. X, dated Jan. 30, 2023 (Jan. 30, 2023)—7 pages (English translation—8 pages).

(Continued)

*Primary Examiner* — Jacques M Saint Surin
(74) *Attorney, Agent, or Firm* — CM Law; Stephen J. Weed (57) ABSTRACT

Provided are an imaging method and system for residual stress of a basin insulator and a method for preparing a test block. The imaging method includes cutting and preparing a standard industrial sample of a basin insulator and testing the acoustoelastic coefficient of the standard industrial (Continued)

sample; then obtaining the residual stress data of the basin insulator and obtaining the spatial point sound velocity distribution of the basin insulator; finally, obtaining a stress distribution cloud map of the basin insulator by calculation of the attribute value and the coordinate data of a to-be-measured location, and performing reliability verification based on the residual stress data.

14 Claims, 4 Drawing Sheets

(51) Int. Cl.
 *G01N 29/06* (2006.01)
 *G01N 29/07* (2006.01)
 *G01N 29/22* (2006.01)
 *G01N 33/44* (2006.01)
(52) U.S. Cl.
 CPC ........... *G01N 29/07* (2013.01); *G01N 29/227* (2013.01); *G01N 33/442* (2013.01); *G01N 2203/0003* (2013.01); *G01N 2203/0019* (2013.01); *G01N 2203/0048* (2013.01); *G01N 2203/0658* (2013.01); *G01N 2291/011* (2013.01)
(58) Field of Classification Search
 CPC ... G01N 2203/0003; G01N 2203/0019; G01N 2203/0048; G01N 2203/0658; G01N 2291/011
 USPC .......................................................... 73/788
 See application file for complete search history.

(56) References Cited

U.S. PATENT DOCUMENTS

| | | | |
|---|---|---|---|
| 6,234,020 B1 | 5/2001 | Haszler et al. | |
| 6,339,958 B1* | 1/2002 | Tsui | G01N 19/04 73/827 |
| 2006/0130586 A1 | 6/2006 | Messer et al. | |
| 2011/0056298 A1 | 3/2011 | O'keefe et al. | |
| 2011/0185814 A1 | 8/2011 | Piccolo | |
| 2015/0035950 A1 | 2/2015 | Kontsos et al. | |
| 2021/0396652 A1 | 12/2021 | Guo et al. | |

FOREIGN PATENT DOCUMENTS

| | | | | |
|---|---|---|---|---|
| CN | 110243935 | A | 9/2019 | |
| CN | 111521309 | A | 8/2020 | |
| CN | 111879858 | A | 11/2020 | |
| CN | 112033588 | A | 12/2020 | |
| CN | 113654702 | A | 11/2021 | |
| CN | 113686965 | A | 11/2021 | |
| CN | 113720922 | A | 11/2021 | |
| CN | 112033588 | * | 4/2022 | .............. G01L 1/25 |
| CN | 114295265 | * | 4/2022 | .............. G01L 1/25 |
| CN | 115372471 | A | 11/2022 | |
| CN | 115420407 | A | 12/2022 | |
| CN | 115470672 | A | 12/2022 | |
| CN | 115629130 | A | 1/2023 | |
| FR | 2930034 | A1 | 10/2009 | |
| JP | 2005195495 | A | 7/2005 | |
| KR | 101955440 | B1 | 3/2019 | |
| WO | 2019148758 | A1 | 8/2019 | |

OTHER PUBLICATIONS

International Search Report for International Application No. PCT/CN2023/123348, dated Dec. 8, 2023 (Dec. 8, 2023)—2 pages (English translation—4 pages).

* cited by examiner

IMAGING METHOD AND SYSTEM FOR RESIDUAL STRESS OF BASIN INSULATOR, AND METHOD FOR PREPARING TEST BLOCK

CROSS-REFERENCE TO RELATED APPLICATIONS

This is a National Stage Application, filed under 35 U.S.C. 371, of International Patent Application No. PCT/CN2023/123348, filed on Oct. 8, 2023, which claims priority to Chinese Patent Application No. 202211644860.X filed with the China National Intellectual Property Administration (CNIPA) on Dec. 21, 2022, the disclosures of which are incorporated herein by reference in their entireties.

TECHNICAL FIELD

The present application relates to the field of high-voltage power transmission technology, for example, an imaging method and system for residual stress of a basin insulator and a method for preparing a test block.

BACKGROUND

As the voltage level of transmission lines in the national power system continues to increase, the size of epoxy resin insulators in gas-insulated switchgears (GISs) and gas-insulated transmission lines (GILs) continues to increase, and the reliability requirements for the epoxy resin insulators are greatly improved. Basin insulators are important support and insulation structures in the GISs and GILs. However, in the pouring process of a basin insulator, the epoxy resin and a curing agent undergo a strong cross-linking reaction and cause curing shrinkage, and a relatively large thermal strain occurs in the cooling stage. As a result, relatively large residual stress is generated inside the insulators. Moreover, the existing factory inspection lacks corresponding type tests and standards, which seriously affects the mechanical reliability of the basin insulators under operating conditions.

Conventional methods for detecting residual stress may be roughly divided into destructive and non-destructive methods. The destructive method such as a blind-hole method may destroy the exterior structure of the insulators and therefore cannot be applied to residual stress monitoring of the insulators. The non-destructive method such as an X-ray diffraction method is primarily used for crystalline materials. The method based on the acoustoelastic effect can effectively detect the residual stress. However, the current manual detection method is time-consuming and labor-intensive, the detection integration coupling is low, and the accuracy cannot be ensured. Therefore, it is difficult to meet the detection requirements for the residual stress of epoxy resin basin insulators.

SUMMARY

The present application proposes an imaging method and system for residual stress of a basin insulator and a method for preparing a test block.

Embodiments of the present application provide an imaging method for residual stress of a basin insulator. The method includes the following:

A standard test block is prepared by cutting a basin insulator from the same batch and performing stress relief annealing repeatedly on the basin insulator, and an acoustoelastic coefficient of the standard test block is obtained.

Residual stress data of the basin insulator are acquired; based on the acoustoelastic coefficient, ultrasonic sound velocities of a spatial point of the basin insulator at different frequencies are tested, and a stress distribution cloud map of the basin insulator is calculated and acquired.

Reliability verification is performed based on the residual stress data.

The step of testing, based on the acoustoelastic coefficient, the ultrasonic sound velocities of the spatial point of the basin insulator at the different frequencies and calculating and acquiring the stress distribution cloud map of the basin insulator includes the following:

A square calculation area is divided along the outer diameter of the basin insulator.

Based on the residual stress data of the basin insulator, an attribute value corresponding to coordinate data of a to-be-measured location in the square calculation area is calculated, a calculation formula of the attribute value is as follows: $Z_p = G_p W$, where p denotes the to-be-measured location, $Z_p$ is the attribute value of the point p, $72 \geq P \geq 1$, $G_p$ is a Green's function matrix of the point p, and W is a weight matrix.

The stress distribution cloud map of the basin insulator is obtained based on the attribute value and the coordinate data of the to-be-measured location.

Embodiments of the present application also provide an imaging system for residual stress of a basin insulator. The system includes a pre-processing module, a calculation module, and a verification module.

The pre-processing module is configured to prepare a standard test block by cutting a basin insulator from the same batch and performing annealing repeatedly on the basin insulator and obtain an acoustoelastic coefficient of the standard test block.

The calculation module is configured to acquire residual stress data of the basin insulator, test ultrasonic sound velocities of a spatial point of the basin insulator at different frequencies based on the acoustoelastic coefficient, and calculate and acquire a stress distribution cloud map of the basin insulator.

The verification module is configured to perform reliability verification based on the residual stress data.

The calculation module includes a division submodule, a calculation submodule, and an imaging submodule.

The division submodule is configured to divide a square calculation area along the outer diameter of the basin insulator.

The calculation submodule is configured to calculate, based on the residual stress data of the basin insulator, an attribute value corresponding to coordinate data of a to-be-measured location in the square calculation area; a calculation formula of the attribute value is as follows: $Z_p = G_p W$; in the formula, p denotes the to-be-measured location, $Z_p$ is an attribute value of the point p, $72 \geq P \geq 1$, $G_p$ is a Green's function matrix of the point p, and W is a weight matrix.

The imaging submodule is configured to obtain the stress distribution cloud map of the basin insulator based on the attribute value and the coordinate data of the to-be-measured location.

Embodiments of the present application also provide a method for preparing a test block. The method is used for preparing the preceding standard test block and includes the following:

A basin insulator from the same batch is selected, a rectangular standard test block is cut from the basin insulator, and the size requirement is that both the length and the width are no less than 40 mm, and the height is no less than 10 mm.

Stress relief annealing is performed on the standard test block, where the stress relief annealing includes placing the standard test block in an industrial oven, raising the oven to 100° C. at a heating rate of 5 k/min and holding for 1 hour, and cooling the oven to the room temperature at a rate of 5 k/min and holding for 20 minutes; and the stress relief annealing is performed twice.

The standard test block is placed in the outdoor environment for 20 days for natural aging treatment.

BRIEF DESCRIPTION OF DRAWINGS

To illustrate the technical schemes in the embodiments of the present application or the technical schemes in the existing art, drawings used in the description of the embodiments or the existing art will be briefly described below. The drawings described below illustrate part of the embodiments of the present application, and those skilled in the art may obtain other drawings based on the drawings described below on the premise that no creative work is done.

DETAILED DESCRIPTION

Embodiments of the present application will be described in conjunction with the drawings in the embodiments of the present application. The embodiments described below are part, not all, of the embodiments of the present application. Based on the embodiments of the present application, all other embodiments obtained by those of ordinary skill in the art without creative work are within the scope of the present application.

Figure 1:
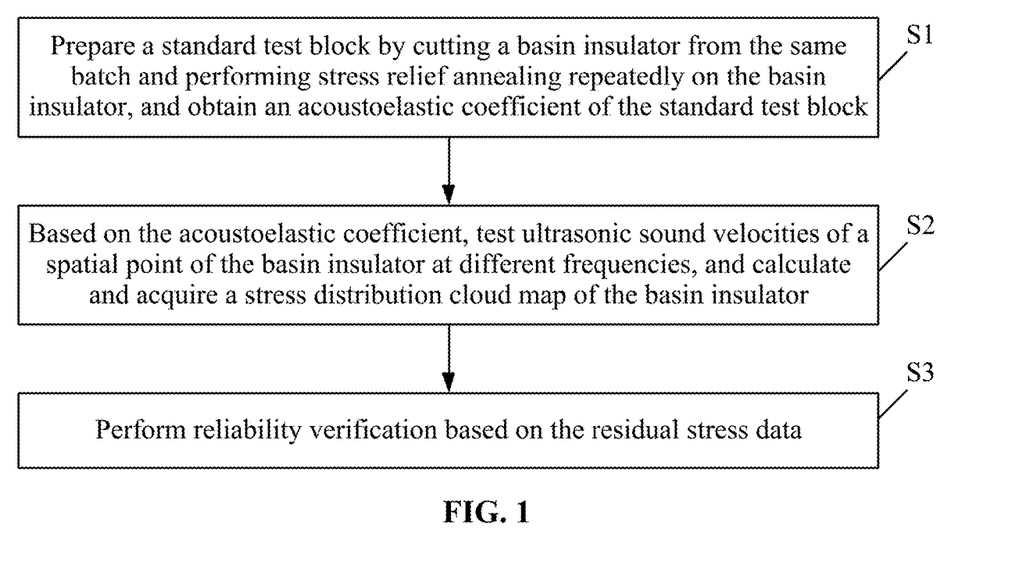
FIG. 1 shows a flowchart of an analysis method for stress of a basin insulator according to the present application.

Embodiments of the present application provide an imaging method for residual stress of a basin insulator. As shown in FIG. 1, the method includes the following steps:

In S1, a standard test block is prepared by cutting a basin insulator from the same batch and performing stress relief annealing repeatedly on the basin insulator, and an acoustoelastic coefficient of the standard test block is obtained.

In S2, based on the acoustoelastic coefficient, ultrasonic sound velocities of a spatial point of the basin insulator are tested at the different frequencies, and a stress distribution cloud map of the basin insulator is calculated and acquired, which includes the following:

In S201, residual stress data of the basin insulator are acquired.

In S202, a square calculation area is divided along the outer diameter of the basin insulator, the number of interpolation points is expanded to 10 times the side length, and calculations are performed based on 72 groups of residual stress data according to a biharmonic spline interpolation function algorithm.

In S203, based on the residual stress data of the basin insulator, an attribute value corresponding to coordinate data of a to-be-measured location in the square calculation area is calculated. The following is included:

Coordinate data of 72 points are converted into a coordinate matrix, denoted as follows: $X=[x_1, x_2, \ldots, x_k]^T$; and $Y=[y_1, y_2, \ldots, y_k]^T$. The attribute value corresponds to a matrix $Z$, $Z=[z_1, z_2, \ldots, z_k]^T$, and $k \leq 72$.

Then a Green's function matrix of order k is denoted as G, as shown below.

$$G = \begin{bmatrix} d_{11} & d_{12} & \ldots & d_{1k} \\ d_{21} & d_{22} & & d_{2k} \\ \vdots & & \ddots & \vdots \\ d_{k1} & k_{k2} & \ldots & d_{kk} \end{bmatrix},$$

$$d_{ij} = \begin{cases} 0, & \text{when } r_{ij} = 0 \\ [\ln(r_{ij}) - 1.0]r_{ij}^2, & \text{when } r_{ij} \neq 0 \end{cases};$$

$i = 1, \ldots, k; j = 1, \ldots, k;$ and $r_{ij} = \sqrt{(x_i - x_j)^2 + (y_i - y_j)^2}$.

where

The weight matrix is denoted as W, and $W = G^{-1}Z$.

The $(1 \times k)$-order Green's function matrix $G_p$ of the point p is calculated, $k \geq p \geq 1$, and $G_p = [d_{p1}, d_{p2}, \ldots, d_{pk}]$.

Finally, the attribute value $Z_p$ of the point p is obtained.

Figure 2:
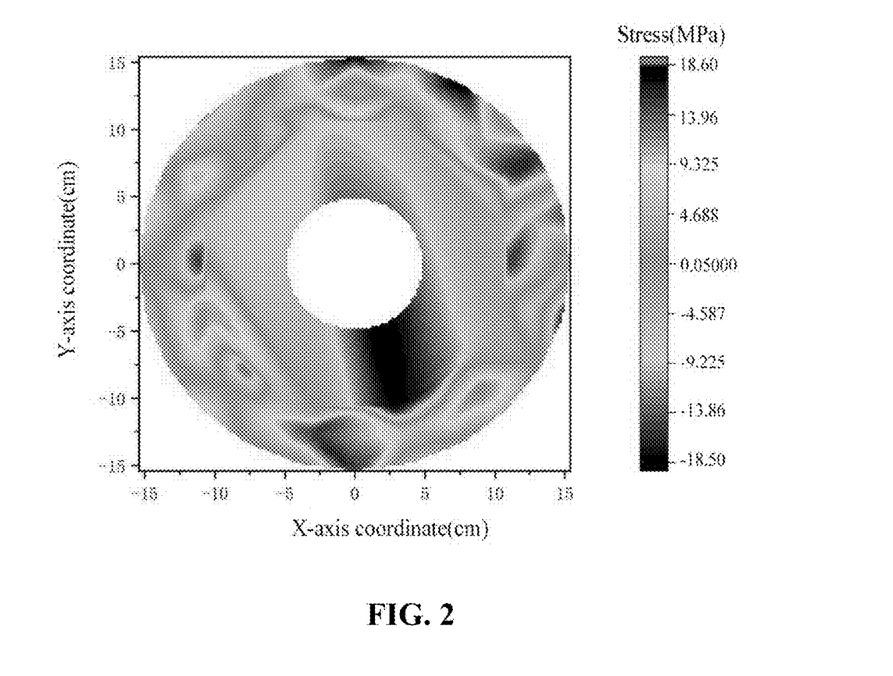
FIG. 2 shows a residual stress cloud map according to the present application.

The calculation formula of the attribute value is as follows: $Z_p = G_p W$, where p denotes the to-be-measured location, $Z_p$ is the attribute value of the point p, $72 \geq P \geq 1$, $G_p$ is the Green's function matrix of the point p, and W is a weight matrix. For example, the coordinate data of 72 points are used as an example. 72 attribute values corresponding to the coordinate data of 72 points are calculated, respectively. Each attribute value corresponds to the stress value at one piece of coordinate data, thus the stress distribution cloud map as shown in FIG. 2 is obtained. The data in areas other than the geometric dimensions of the insulator are removed. In the figure, a positive stress value represents tensile stress, and a negative value represents compressive stress.

In S204, the stress distribution cloud map of the basin insulator is obtained based on the attribute value and the coordinate data of the to-be-measured location.

In S3, reliability verification is performed based on the residual stress data, which includes the following:

In S301, three strain gauges are installed on the to-be-measured location of the basin insulator, an included angle between the three strain gauges at each point is 45°; a strain change of the basin insulator after drilling is measured, and an exact value and a direction of a verification stress at the point is calculated according to the following formula:

$$\begin{cases} \sigma_1 = \frac{E}{4K_1}(\varepsilon_1 + \varepsilon_3) - \frac{E}{4K_2}\sqrt{(\varepsilon_1 - \varepsilon_2)^2 + (2\varepsilon_2 - \varepsilon_1 - \varepsilon_3)^2} \\ \sigma_2 = \frac{E}{4K_1}(\varepsilon_1 + \varepsilon_3) + \frac{E}{4K_2}\sqrt{(\varepsilon_1 - \varepsilon_2)^2 + (2\varepsilon_2 - \varepsilon_1 - \varepsilon_3)^2} \\ \tan 2\theta = \frac{2\varepsilon_2 - \varepsilon_1 - \varepsilon_3}{\varepsilon_1 + \varepsilon_3} \end{cases}.$$

$\varepsilon_1$, $\varepsilon_2$, and $\varepsilon_3$ are strains measured by the strain gauges respectively in the horizontal direction, a 45° oblique direction, and the vertical direction. $K_1$ and $K_2$ are stress release coefficients of the insulator. E is the material elastic modulus. θ is an angle between the maximum principal stress and a strain gauge 1. $\sigma_1$ is the maximum verification stress. $\sigma_2$ is the minimum verification stress.

In S302, the maximum verification stress and the minimum verification stress are separately compared with the obtained residual stress data of the to-be-measured location of the basin insulator; and if the relative errors are all within 10%, it is confirmed that the residual stress data are accurate.

It should be noted that the initial state of the standard test block may be regarded as no residual stress inside the block. The sample is a block sample, and the basin insulator has a basin structure. Additionally, when the stress distribution cloud map is obtained, the corresponding stress value may be calculated according to the coordinates of each measurement location, and a mechanical reliability risk coefficient n of the basin insulator may be determined. The formula of n is as follows:

$$\eta = \begin{cases} \frac{\sigma_m}{\sigma_T}, & \sigma_m > 0 \\ 0, & \sigma_m \leq 0 \end{cases}.$$

$\sigma_m$ is a calculated stress value. $\sigma_T$ is the tensile strength of the material.

Figure 3:
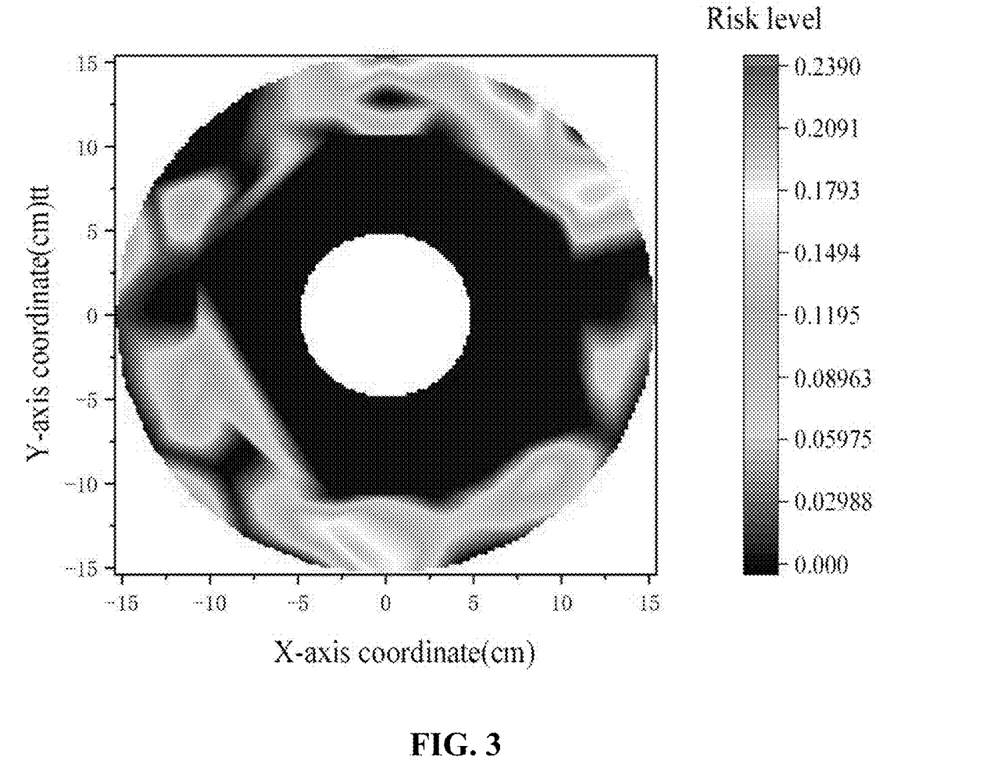
FIG. 3 shows the risk level of residual stress according to the present application.

The same interpolation fitting method in the preceding steps is applied to the risk coefficient n, and the risk coefficient cloud map of the residual stress of the basin insulator is drawn, as shown in FIG. 3. The risk value has a range of 0 to 1.

In an embodiment, the step of obtaining the acoustoelastic coefficient of the standard test block may include the following:

Different pressures are applied to the standard test block; the pressure is greater than or equal to 0.

An ultrasonic wave of a set frequency is sent to the standard test block under different pressures, and propagation time is obtained; the propagation time is the propagation time of the ultrasonic wave in the standard test block under different pressures.

The propagation velocity of the ultrasonic wave is obtained based on the propagation distance and the propagation time of the ultrasonic wave in the standard test block under different pressures.

The acoustoelastic coefficient is obtained based on the propagation velocity of the ultrasonic wave.

It should be noted that in a process of measuring the acoustoelastic coefficient of the standard test block, the ultrasonic wave enters the standard test block at the set frequency until the ultrasonic wave hits the wall of the standard test block to rebound, and then returns to the position where the ultrasonic wave is emitted; additionally, the propagation velocity of the ultrasonic wave inside the standard test block is different if the pressure applied to the standard test block is different. By the collection and analysis of data of the propagation time under different pressures, the acoustoelastic coefficient may be calculated according to the formula of the acoustoelastic equation. For example, the formula of the acoustoelastic coefficient is as follows:

$$\frac{V - V_0}{V_0} = K\sigma.$$

$V_0$ is the propagation velocity of the ultrasonic wave in the sample under a pressure equal to zero; V is the propagation velocity of the ultrasonic wave in the sample under a pressure greater than zero; K is the acoustoelastic coefficient; and σ is the residual stress of the standard test block under different pressures.

In an embodiment, the step of acquiring the residual stress data of the basin insulator may include the following:

A coordinate origin is set.

Multiple to-be-measured locations are selected on the surface of the basin insulator, and based on the coordinate origin, coordinate data of the multiple to-be-measured locations are acquired.

Generally, a circle of equally-spaced 24 points with different heights, 72 points of to-be-measured locations in total, are pre-calibrated on the surface of the basin insulator, and the spatial geometric location of each point is determined according to the size of the basin insulator.

A waveform of the ultrasonic wave at each to-be-measured location is measured based on the coordinate data.

A to-be-measured velocity at each to-be-measured location is obtained based on the waveform of the ultrasonic wave at the to-be-measured location and the propagation distance of the ultrasonic wave in the basin insulator; the to-be-measured velocity is the propagation velocity of the ultrasonic wave in the basin insulator.

Residual stress data of each to-be-measured location are obtained based on the to-be-measured velocity of the ultrasonic wave at the to-be-measured location and the acoustoelastic coefficient. For example, after the measurement of 72 points, the software is called to convert the waveforms of 72 points into a text document by batch processing, then the peak values of the primary echo and the secondary echo in the waveforms are screened out, and the time difference between the two echoes is the propagation time t of the ultrasonic signal in the sound path of the double thickness L of the basin insulator. The formula is as follows:

$V_{measurement} = 2L/t$, where $V_{measurement}$ is the to-be-measured velocity.

Via the preceding formula, the to-be-measured velocity corresponding to each of the 72 points on the basin insulator may be calculated, then the stress distribution at each measurement point may be automatically calculated via the formula of the acoustoelastic coefficient, and the stress value at each point is stored in a matrix form based on the location information.

Figure 4:
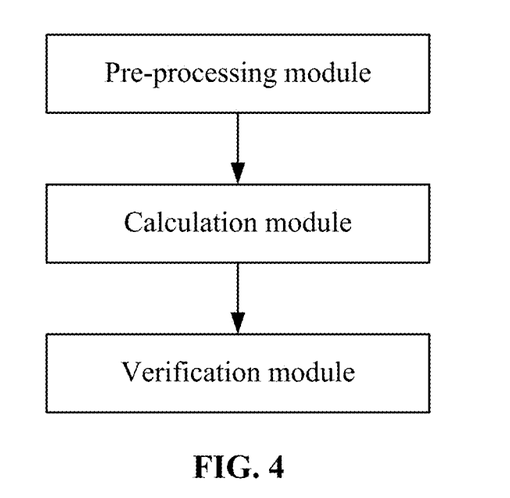
FIG. 4 shows a structure diagram of an analysis system for the stress of a basin insulator according to the present application.

Embodiments of the present application also provide an imaging system for residual stress of a basin insulator. As shown in FIG. 4, the system includes a pre-processing module, a calculation module, and a verification module. The pre-processing module is configured to prepare a standard test block by cutting a basin insulator from the same batch and performing stress relief annealing repeatedly on the basin insulator and obtain an acoustoelastic coefficient of the standard test block. The calculation module is configured to acquire residual stress data of the basin insulator, test ultrasonic sound velocities of a spatial point of the basin insulator at different frequencies based on the acoustoelastic coefficient, and calculate and acquire a stress distribution cloud map of the basin insulator. The verification module is configured to perform reliability verification based on the residual stress data.

In an embodiment, the calculation module includes a division submodule, a calculation submodule, and an imaging submodule. The division submodule is configured to divide a square calculation area along the outer diameter of the basin insulator. The calculation submodule is configured to calculate, based on the residual stress data of the basin insulator, an attribute value corresponding to coordinate data of a to-be-measured location in the square calculation area; the calculation formula of the attribute value is as follows: $Z_p=G_pW$; in the formula, p denotes the to-be-measured location, $Z_p$ is the attribute value of the point p, $72 \geq P \geq 1$, $G_p$ is a Green's function matrix of the point p, and W is a weight matrix. The imaging submodule is configured to obtain the stress distribution cloud map of the basin insulator based on the attribute value and the coordinate data of the to-be-measured location.

In an embodiment, the pre-processing module includes a pressure submodule, an ultrasound submodule, a measurement submodule, and a construction submodule. The pressure submodule is configured to apply different pressures to the standard test block; each of the pressures is greater than or equal to 0. The ultrasound submodule is configured to send an ultrasonic wave of a set frequency to the standard test block under different pressures and obtain propagation time; the propagation time is the propagation time of the ultrasonic wave in the standard test block under different pressures. The measurement submodule is configured to obtain the propagation velocity of the ultrasonic wave based on the propagation distance and the propagation time of the ultrasonic wave in the standard test block under different pressures. The construction submodule is configured to obtain the acoustoelastic coefficient based on the propagation velocity of the ultrasonic wave.

Figure 5:
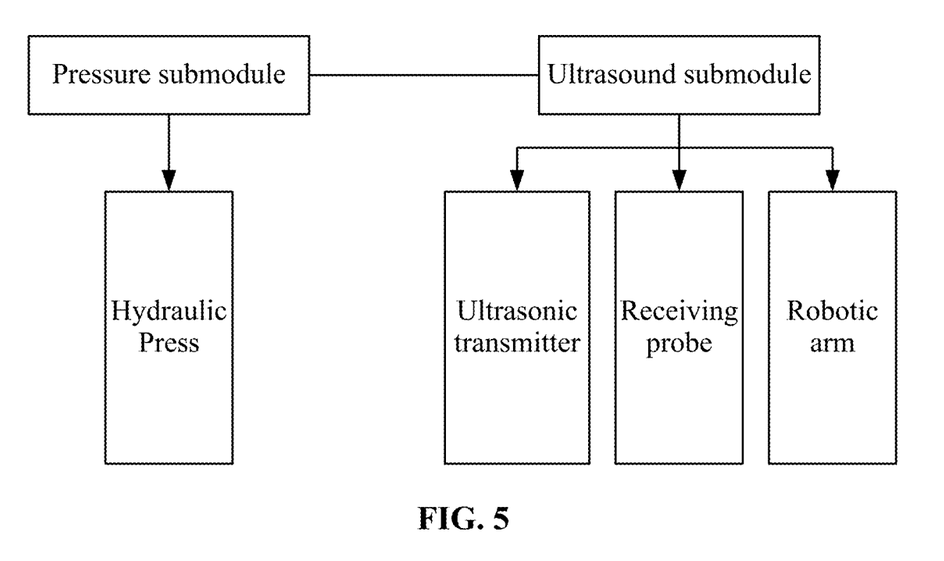
FIG. 5 shows a structure diagram of a pressure module and an ultrasound module according to the present application.

It should be noted that as shown in FIG. 5, the pressure submodule generally uses a hydraulic press to apply the pressures to the basin insulator and the standard test block, while the ultrasound submodule includes an ultrasonic transmitter, a receiving probe, and a robotic arm.

In an embodiment, the calculation module includes a setting submodule, a selection submodule, an acquisition submodule, a calculation submodule, and a data set submodule. The setting submodule is configured to set a coordinate origin. The selection submodule is configured to select multiple to-be-measured locations on the surface of the basin insulator and acquire coordinate data of the multiple to-be-measured locations based on the coordinate origin. The acquisition submodule is configured to measure a waveform of an ultrasonic wave at each to-be-measured location based on the coordinate data. The calculation submodule is configured to obtain the to-be-measured velocity at each to-be-measured location based on the waveform of the ultrasonic wave at the to-be-measured location and the propagation distance of the ultrasonic wave in the basin insulator; the to-be-measured velocity is the propagation velocity of the ultrasonic wave in the basin insulator. The data set submodule is configured to obtain residual stress data of each to-be-measured location based on the to-be-measured velocity at the to-be-measured location and the acoustoelastic coefficient.

It should be noted that setting the origin location means initialization of the location of the robotic arm using this point as the origin via the host computer. Additionally, an oscilloscope needs to be connected to the computer before the origin is set, and the computer is used for observing the waveform online. When acquiring the waveform, the acquisition submodule needs to enter the spatial coordinates of the to-be-measured location into the host computer of the robotic arm, use a delay command to make the robotic arm hold and stop the receiving probe stably for 20 seconds at each measurement point, and automatically save the waveform after a detected waveform stabilizes.

Figure 6:
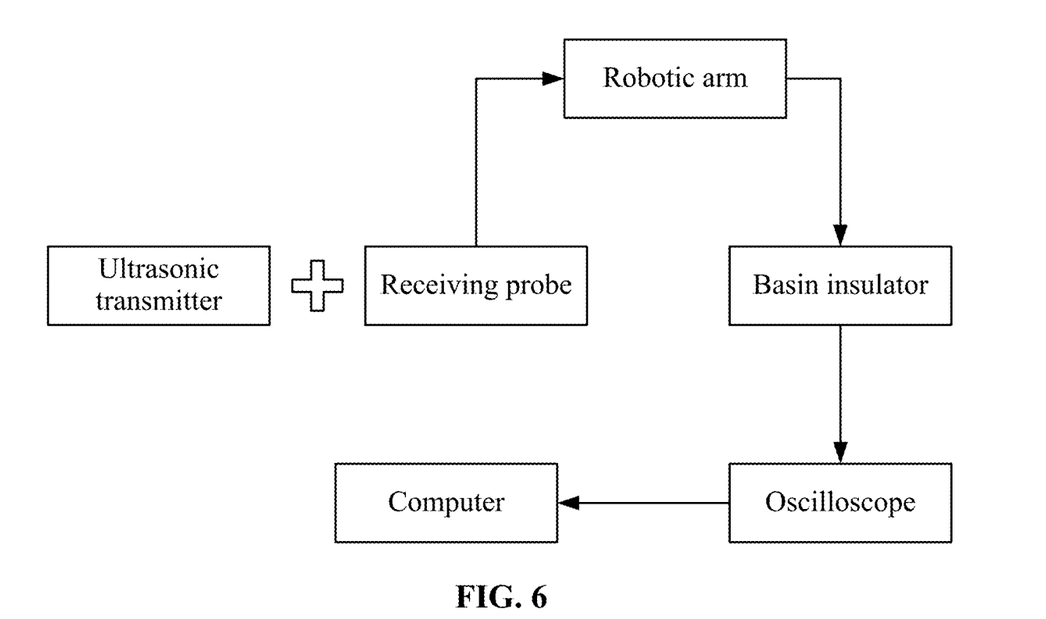
FIG. 6 is a schematic flowchart of an ultrasonic transmitter, a receiving probe, a robotic arm, an oscilloscope, and a computer according to the present application.

As shown in FIG. 6, the ultrasonic transmitter and the receiving probe are integrated structures and are integrally installed on the robotic arm; the robotic arm automatically scans the basin insulator via the ultrasonic transmitter and receiving probe to obtain the ultrasonic propagation velocity inside the basin insulator at each location, then the collected data are transmitted to the oscilloscope to obtain a stable waveform, and finally the ultrasonic propagation time is extracted by the computer.

Figure 7:
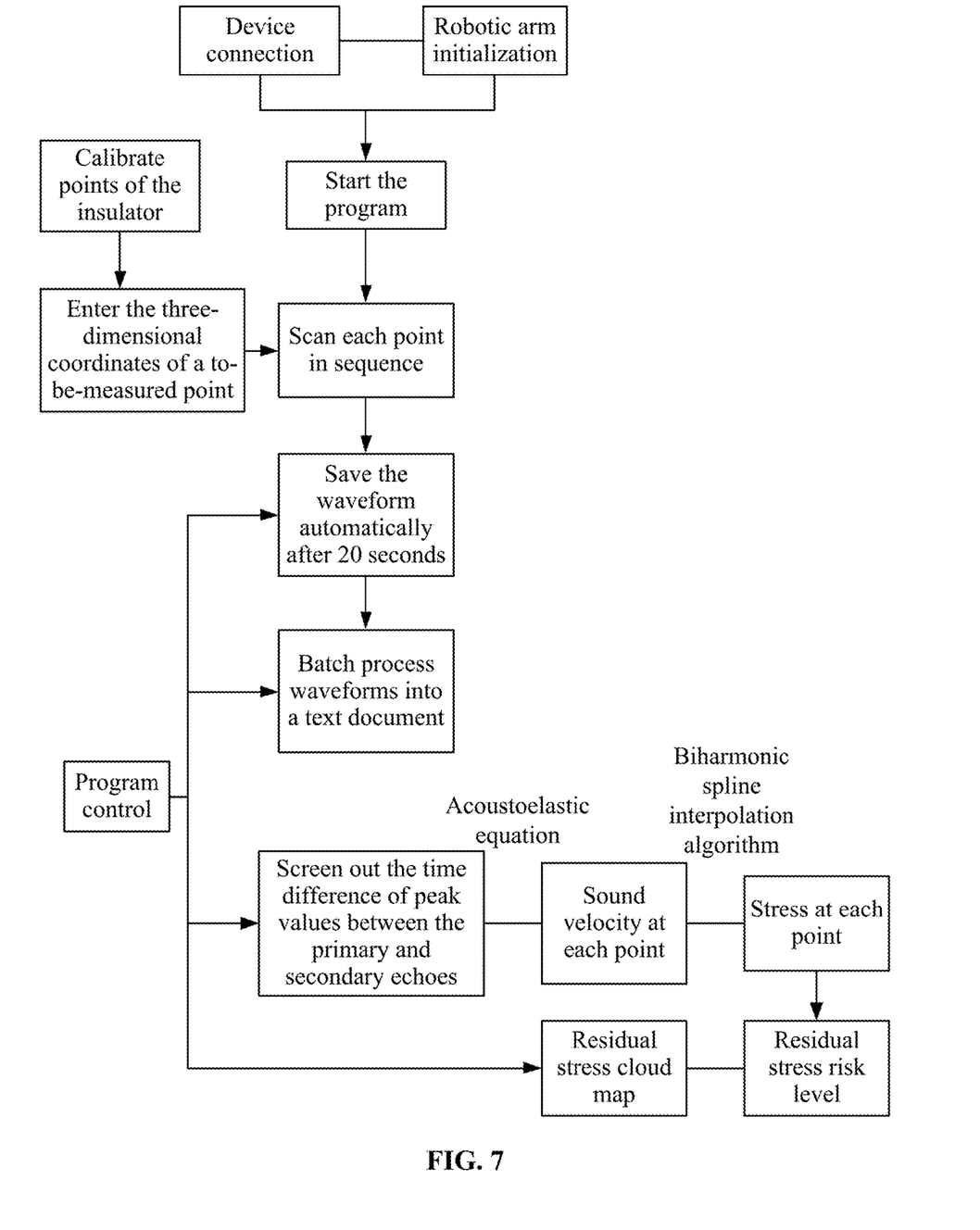
FIG. 7 is a working flowchart of an analysis system for the stress of a basin insulator according to the present application.

As shown in FIG. 7, during operation of the system, the following steps may be included:

Before the program is started, on the one hand, the devices are connected, the location of the robotic arm is initialized to set the origin; on the other hand, coordinates are calibrated on the basin insulator and entered into the host computer of the robotic arm.

Subsequently, the program is started; the robotic arm carries the ultrasonic probe to scan the surface of the basin insulator and holds at each point for 20 seconds to obtain a stable waveform, and the waveform is processed into a text document; then the peak values of the primary echo and the secondary echo in the waveform are screened out to obtain the ultrasonic propagation time. The ultrasonic propagation velocity is calculated according to the thickness of the basin insulator and the ultrasonic propagation time. The stress at each point is calculated via the acoustoelastic coefficient, and then the overall stress of the basin insulator is fitted via the biharmonic spline interpolation method, thereby obtaining the residual stress cloud map and residual stress risk coefficient.

Optionally, the verification module includes a first verification submodule and a second verification submodule.

The first verification submodule is configured to install three strain gauges on the to-be-measured location of the basin insulator, measure the strain change of the basin insulator after drilling, and calculate an exact value and a direction of verification stress at the to-be-measured location; an included angle between the three strain gauges at each point is 45°.

The second verification submodule is configured to separately compare the maximum verification stress and the minimum verification stress with the obtained residual stress data of the to-be-measured location of the basin insulator; and if the relative errors are all within 10%, the second verification submodule is configured to confirm that the residual stress data are accurate.

It should be noted that the material of the basin insulator includes epoxy resin, micron alumina, and a solid curing agent.

In view of the lack of simple and highly automated detection methods for the internal residual stress of epoxy resin basin insulators in the related art, the present application proposes a method for rapid detection and imaging of internal residual stress in a basin insulator based on the acoustoelastic effect. The overall apparatus consists of a robotic arm, an ultrasonic transmitter, an oscilloscope, an ultrasonic transceiver probe, and a computer. First, a standard test block for an epoxy resin basin insulator is prepared according to the same raw material ratio, and the acoustoelastic coefficient and the basic sound velocity of the epoxy insulation material are measured. Then, the spatial motion path of the robotic arm is programmed according to the geometric dimensions of the basin insulator, the ultrasonic probe and the robotic arm are fixed, and automatic scanning detection of 72 points on the outer surface of the basin insulator is completed. The collected sound velocity signals are converted into stress data via the acoustoelastic equation. The residual stress distribution cloud map of the basin insulator is generated by using computer software through a biharmonic spline interpolation algorithm, and the risk of the internal residual stress of the basin insulator is analyzed and evaluated according to the tensile strength of the material. The entire system has a high degree of automation, which can reduce the impact of human factors on test results. Moreover, the measurement results are intuitive and clear.

A method for preparing a basin insulator standard sample (or standard test block) in this system and method is described below. The method may include the following steps:

In A1, a basin insulator from the same batch is selected, a rectangular standard test block is cut from the basin insulator, and the size requirement is that both the length and the width are no less than 40 mm, and the height is no less than 10 mm.

In A2, stress relief annealing is performed on the standard test block, where the standard test block is placed in an industrial oven, the oven is raised to 100° C. at a heating rate of 5 k/min and held for 1 hour, then the oven is cooled to the room temperature at the rate of 5 k/min and held for 20 min; and the preceding stress relief annealing is performed twice.

In A3, the standard test block is placed in an outdoor environment for 20 days for natural aging treatment.

It should be noted that a standard test block of epoxy resin composite material prepared from a sample taken from an insulator of the same batch as the basin insulator is used, and the standard test block can be considered to be free of internal residual stress since the standard test block has a small volume and is subjected to the stress relief annealing and natural aging treatment.

Additionally, the test block may also be prepared by the following method:

In B1, a mold for the standard test block of the basin insulator is selected, and the mold is pre-treated. For example, the pre-treatment may include spraying a release agent on the inner surface of the mold and leaving the mold in a fume hood for 5 minutes.

In B2, the epoxy resin, alumina powder, solid curing agent, and mold are pre-heated in an industrial oven, where the pre-heating temperature is 100° C., and the pre-heating time is 1 hour.

In B3, after the pre-heating is completed, the epoxy resin and the alumina powder are mixed and stirred, and then a curing agent is added and stirred again so that the mixture is well stirred; after being well stirred, the mixture is put into a rotary vacuum pump for two times of vacuum deforming with a total duration of 20 minutes. The mass ratio of the epoxy resin, curing agent, and alumina powder is 100:44:306.

In B4, the mixture is poured into the pre-heated mold, and the mold is placed in the oven for curing, cooled to the room temperature after the completion of curing, and then de-molded; the curing temperature is 140° C., and the curing time is 14 hours.

The present application includes at least the following beneficial effects:

1. In the analysis method and system of the basin insulator stress according to the present application, an industrial robotic arm is used for clamping an ultrasonic probe to pre-calibrate the location according to the size of the basin insulator sample, and then scanning and ultrasonic testing are performed. The collected data are processed and analyzed by using a computer to obtain the residual stress distribution map of the basin insulator sample, and an insulator reliability cloud map is given in combination with the strength theory. The present application improves the accuracy of detection results without damaging the structure of the basin insulator and has a high degree of automation. Thus, the present application can be effectively used in factory inspection of epoxy resin insulators.

2. The present application also proposes a method for verifying the accuracy of residual stress after obtaining the residual stress data. By using the strain gauges to perform error verification on the basin insulation samples, the accuracy of stress measurement using the ultrasonic wave is verified.

3. The present application uses the same industrial material formula as the basin insulator to cast the standard sample of epoxy resin composite material. The standard sample has a small volume and is uniformly heated, the curing time is relatively short, and the cooling time is prolonged. Thus, it can be considered that no residual stress is inside the standard sample. A hydraulic press is used for applying different pressure loads to the epoxy resin standard test block, and the sound velocity is measured so that the sound velocity-stress corresponding functional relationship is obtained, and then the acoustoelastic coefficient is obtained, thereby providing a basic parameter for subsequent residual stress detection.

4. The present application first measures and calibrates the geometric parameters of a tested part, writes a scanning path for the industrial robotic arm to achieve the function of automatically transmitting and receiving ultrasonic signals at each to-be-measured point of the tested basin insulator sample, and uses the acoustoelastic effect equation to obtain the magnitude and location information of the residual stress corresponding to the sound velocity and store the information in a matrix form. Thus, batch testing of the basin insulator samples of the same type is achieved, and system errors caused by human factors are reduced.

What is claimed is:

1. An imaging method for residual stress of a basin insulator, comprising:
preparing a standard test block by cutting a basin insulator from a same batch and performing stress relief annealing repeatedly on the basin insulator, and obtaining an acoustoelastic coefficient of the standard test block;
wherein obtaining the acoustoelastic coefficient of the standard test block comprises:
applying different pressures to the standard test block, wherein each of the different pressures is greater than or equal to 0; and
sending an ultrasonic wave of a set frequency to the standard test block under the different pressures and obtaining propagation time, wherein the propagation time is propagation time of the ultrasonic wave in the standard test block under the different pressures, and obtaining the propagation time comprises: scanning, by an ultrasonic probe carried by a robotic arm, a surface of the standard test block to obtain a waveform, and after the waveform is processed into a text document, screening out peak values of a primary echo and a secondary echo in the waveform to obtain the propagation time;
obtaining a propagation velocity of the ultrasonic wave based on a propagation distance and the propagation time of the ultrasonic wave in the standard test block under the different pressures; and
obtaining the acoustoelastic coefficient based on the propagation velocity of the ultrasonic wave;

testing, based on the acoustoelastic coefficient, ultrasonic sound velocities of a spatial point of the basin insulator at different frequencies, and calculating and acquiring a stress distribution cloud map of the basin insulator,
wherein testing, based on the acoustoelastic coefficient, the ultrasonic sound velocities of the spatial point of the basin insulator at the different frequencies, and calculating and acquiring the stress distribution cloud map of the basin insulator comprise:
acquiring residual stress data of the basin insulator;
dividing a square calculation area along an outer diameter of the basin insulator;
calculating, based on the residual stress data of the basin insulator, an attribute value corresponding to coordinate data of a to-be-measured location in the square calculation area, wherein a calculation formula of the attribute value is as follows: $Z_p = G_p W$, where p denotes the to-be-measured location, $Z_p$ is an attribute value of the point p, $72 \geq P \geq 1$, $G_p$ is a Green's function matrix of the point p, and W is a weight matrix; and
obtaining the stress distribution cloud map of the basin insulator based on the attribute value and the coordinate data of the to-be-measured location; and
performing reliability verification based on the residual stress data.

2. The imaging method for residual stress of a basin insulator according to claim 1, wherein a formula of the acoustoelastic coefficient is as follows:

$$\frac{V - V_0}{V_0} = K\sigma;$$

wherein $V_0$ is a propagation velocity of the ultrasonic wave in the standard test block under a pressure equal to zero, V is a propagation velocity of the ultrasonic wave in the standard test block under a pressure greater than zero; K is the acoustoelastic coefficient, and σ is residual stress of the standard test block under different pressures.

3. The imaging method for residual stress of a basin insulator according to claim 2, wherein acquiring the residual stress data of the basin insulator comprises:
setting a coordinate origin;
selecting a plurality of to-be-measured locations on a surface of the basin insulator, and acquiring coordinate data of the plurality of to-be-measured locations based on the coordinate origin;
measuring a waveform of the ultrasonic wave at each of the plurality of to-be-measured locations based on the coordinate data;
obtaining a to-be-measured velocity of each of the plurality of to-be-measured locations based on the waveform of the ultrasonic wave at the each of the plurality of to-be-measured locations and the propagation distance of the ultrasonic wave in the basin insulator, wherein the to-be-measured velocity is the propagation velocity of the ultrasonic wave in the basin insulator; and
obtaining residual stress data of each of the plurality of to-be-measured locations based on the to-be-measured velocity of each of the plurality of to-be-measured locations and the acoustoelastic coefficient.

4. The imaging method for residual stress of a basin insulator according to claim 1, wherein performing the reliability verification based on the residual stress data comprises:

installing three strain gauges on the to-be-measured location of the basin insulator, wherein an included angle between the three strain gauges at the to-be-measured location is 45°, measuring a strain change of the basin insulator after drilling, and calculating an exact value and a direction of a verification stress at the to-be-measured location according to the following formula:

$$\begin{cases} \sigma_1 = \frac{E}{4K_1}(\varepsilon_1 + \varepsilon_3) - \frac{E}{4K_2}\sqrt{(\varepsilon_1 - \varepsilon_2)^2 + (2\varepsilon_2 - \varepsilon_1 - \varepsilon_3)^2} \\ \sigma_2 = \frac{E}{4K_1}(\varepsilon_1 + \varepsilon_3) + \frac{E}{4K_2}\sqrt{(\varepsilon_1 - \varepsilon_2)^2 + (2\varepsilon_2 - \varepsilon_1 - \varepsilon_3)^2} \\ \tan 2\theta = \frac{2\varepsilon_2 - \varepsilon_1 - \varepsilon_3}{\varepsilon_1 + \varepsilon_3} \end{cases} ;$$

wherein $\varepsilon_1$, $\varepsilon_2$, and $\varepsilon_3$ are strains measured by the three strain gauges respectively in a horizontal direction, a 45° oblique direction, and a vertical direction, $K_1$ and $K_2$ are stress release coefficients of the insulator, E is a material elastic modulus, θ is an angle between a maximum principal stress and one gauge of the three strain gauges, $\sigma_1$ is a maximum verification stress, and $\sigma_2$ is a minimum verification stress; and
comparing the maximum verification stress and the minimum verification stress separately with obtained residual stress data of the to-be-measured location of the basin insulator, and in response to determining that a relative error between the maximum verification stress and the residual stress data is within 10% and a relative error between the minimum verification stress and the residual stress data is within 10%, confirming that the residual stress data are accurate.

5. An imaging system for residual stress of a basin insulator, configured to execute the imaging method for residual stress of a basin insulator according to claim 1 and comprising a pre processing module, a calculation module, and a verification module; wherein
the pre processing module is configured to prepare a standard test block by cutting a basin insulator from a same batch and performing stress relief annealing repeatedly on the basin insulator and obtain an acoustoelastic coefficient of the standard test block;
the calculation module is configured to test ultrasonic sound velocities of a spatial point of the basin insulator at different frequencies based on the acoustoelastic coefficient, and calculate and acquire a stress distribution cloud map of the basin insulator; and
the verification module is configured to perform reliability verification based on the residual stress data;
wherein the calculation module comprises an acquisition submodule, a division submodule, a calculation submodule, and an imaging submodule; wherein
the acquisition submodule is configured to acquire residual stress data of the basin insulator;
the division submodule is configured to divide a square calculation area along an outer diameter of the basin insulator;
the calculation submodule is configured to calculate, based on the residual stress data of the basin insulator, an attribute value corresponding to coordinate data of a to-be-measured location in the square calculation area, wherein a calculation formula of the attribute value is as follows: $Z_p = G_p W$; where p denotes the to-be-measured location, $Z_p$ is an attribute value of the point p, $72 \geq P \geq 1$, $G_p$ is a Green's function matrix of the point p, and W is a weight matrix; and the imaging submodule is configured to obtain the stress distribution cloud map of the basin insulator based on the attribute value and the coordinate data of the to-be-measured location.

6. The imaging system for residual stress of a basin insulator according to claim 5, wherein the pre processing module comprises a pressure submodule, an ultrasound submodule, a measurement submodule, and a construction submodule; wherein
the pressure submodule is configured to apply different pressures to the standard test block, wherein each of the different pressures is greater than or equal to 0;
the ultrasound submodule is configured to send an ultrasonic wave of a set frequency to the standard test block under the different pressures and obtain propagation time, wherein the propagation time is propagation time of the ultrasonic wave in the standard test block under the different pressures;
the measurement submodule is configured to obtain a propagation velocity of the ultrasonic wave based on a propagation distance and the propagation time of the ultrasonic wave in the standard test block under the different pressures; and
the construction submodule is configured to obtain the acoustoelastic coefficient based on the propagation velocity of the ultrasonic wave.

7. The imaging system for residual stress of a basin insulator according to claim 5, wherein an acquisition submodule comprises a setting submodule, a selection submodule, an acquisition submodule, a calculation submodule, and a data set submodule; wherein
the setting submodule is configured to set a coordinate origin;
the selection submodule is configured to select a plurality of to-be-measured locations on a surface of the basin insulator, and acquire coordinate data of the plurality of to-be-measured locations based on the coordinate origin;
the acquisition submodule is configured to measure a waveform of an ultrasonic wave at each of the plurality of to-be-measured locations based on the coordinate data;
the calculation submodule is configured to obtain a to-be-measured velocity of each of the plurality of to-be-measured locations based on the waveform of the ultrasonic wave at the each of the plurality of to-be-measured locations and a propagation distance of the ultrasonic wave in the basin insulator, wherein the to-be-measured velocity is a propagation velocity of the ultrasonic wave in the basin insulator; and
the data set submodule is configured to obtain residual stress data of each of the plurality of to-be-measured locations based on the to-be-measured velocity of the each of the plurality of to-be-measured locations and the acoustoelastic coefficient.

8. The imaging system for residual stress of a basin insulator according to claim 5, wherein the verification module comprises a first verification submodule and a second verification submodule; wherein
the first verification submodule is configured to install three strain gauges on the to-be-measured location of the basin insulator, measure a strain change of the basin insulator after drilling, and calculate an exact value and a direction of a verification stress at the to-be-measured location, wherein an included angle between the three strain gauges at each point is 45°; and
the second verification submodule is configured to compare a maximum verification stress and a minimum verification stress separately with obtained residual stress data of the to-be-measured location of the basin insulator; and confirm that the residual stress data are accurate, in response to determining that a relative error between the maximum verification stress and the residual stress data is within 10% and a relative error between the minimum verification stress and the residual stress data is within 10%.

9. The imaging system for residual stress of a basin insulator according to claim 5, wherein a material of the standard test block comprises epoxy resin.

10. The imaging system for residual stress of a basin insulator according to claim 5, wherein the preprocessing module is configured to prepare the standard test block in the following manner:
selecting a basin insulator from a same batch, and cutting a rectangular standard test block from the basin insulator, wherein a size requirement is that both a length and a width of the rectangular standard test block are no less than 40 mm, and a height of the rectangular standard test block is no less than 10 mm;
performing stress relief annealing on the standard test block, wherein the stress relief annealing comprises placing the standard test block in an industrial oven, raising the oven to 100° C. at a heating rate of 5 Kelvin per minute and holding for 1 hour, and cooling the oven to a room temperature at a rate of 5 kelvin per minute and holding for 20 minutes; and performing the stress relief annealing twice; and
placing the standard test block in an outdoor environment for 20 days for natural aging treatment.

11. The imaging system for residual stress of a basin insulator according to claim 6, wherein the preprocessing module is configured to prepare the standard test block in the following manner:
selecting a basin insulator from a same batch, and cutting a rectangular standard test block from the basin insulator, wherein a size requirement is that both a length and a width of the rectangular standard test block are no less than 40 mm, and a height of the rectangular standard test block is no less than 10 mm;
performing stress relief annealing on the standard test block, wherein the stress relief annealing comprises placing the standard test block in an industrial oven, raising the oven to 100° C. at a heating rate of 5 Kelvin per minute and holding for 1 hour, and cooling the oven to a room temperature at a rate of 5 kelvin per minute and holding for 20 minutes; and performing the stress relief annealing twice; and
placing the standard test block in an outdoor environment for 20 days for natural aging treatment.

12. The imaging system for residual stress of a basin insulator according to claim 7, wherein the preprocessing module is configured to prepare the standard test block in the following manner:
selecting a basin insulator from a same batch, and cutting a rectangular standard test block from the basin insulator, wherein a size requirement is that both a length and a width of the rectangular standard test block are no less than 40 mm, and a height of the rectangular standard test block is no less than 10 mm;
performing stress relief annealing on the standard test block, wherein the stress relief annealing comprises placing the standard test block in an industrial oven, raising the oven to 100° C. at a heating rate of 5 Kelvin per minute and holding for 1 hour, and cooling the oven to a room temperature at a rate of 5 kelvin per minute and holding for 20 minutes; and performing the stress relief annealing twice; and placing the standard test block in an outdoor environment for 20 days for natural aging treatment.

13. The imaging system for residual stress of a basin insulator according to claim 8, wherein the preprocessing module is configured to prepare the standard test block in the following manner:

selecting a basin insulator from a same batch, and cutting a rectangular standard test block from the basin insulator, wherein a size requirement is that both a length and a width of the rectangular standard test block are no less than 40 mm, and a height of the rectangular standard test block is no less than 10 mm;

performing stress relief annealing on the standard test block, wherein the stress relief annealing comprises placing the standard test block in an industrial oven, raising the oven to 100° C. at a heating rate of 5 Kelvin per minute and holding for 1 hour, and cooling the oven to a room temperature at a rate of 5 kelvin per minute and holding for 20 minutes; and performing the stress relief annealing twice; and placing the standard test block in an outdoor environment for 20 days for natural aging treatment.

14. The imaging system for residual stress of a basin insulator according to claim 9, wherein the preprocessing module is configured to prepare the standard test block in the following manner:

selecting a basin insulator from a same batch, and cutting a rectangular standard test block from the basin insulator, wherein a size requirement is that both a length and a width of the rectangular standard test block are no less than 40 mm, and a height of the rectangular standard test block is no less than 10 mm;

performing stress relief annealing on the standard test block, wherein the stress relief annealing comprises placing the standard test block in an industrial oven, raising the oven to 100° C. at a heating rate of 5 Kelvin per minute and holding for 1 hour, and cooling the oven to a room temperature at a rate of 5 kelvin per minute and holding for 20 minutes; and performing the stress relief annealing twice; and placing the standard test block in an outdoor environment for 20 days for natural aging treatment.

\* \* \* \* \*